(12) United States Patent
Kagosaki et al.

(10) Patent No.: US 7,559,905 B2
(45) Date of Patent: Jul. 14, 2009

(54) HIFU PROBE FOR TREATING TISSUE WITH IN-LINE DEGASSING OF FLUID

(75) Inventors: Shuhei Kagosaki, Chiba (JP); Yutaka Shimazaki, Tokyo (JP); Kenji Yamashita, Tokyo (JP); Bernard J. Esarey, Defiance, OH (US); Artur P. Katny, Ingalls, IN (US); Ralf Seip, Indianapolis, IN (US); Narendra T. Sanghvi, Indianapolis, IN (US)

(73) Assignee: Focus Surgery, Inc., Indianapolis, IN (US)

( * ) Notice: Subject to any disclaimer, the term of this patent is extended or adjusted under 35 U.S.C. 154(b) by 80 days.

(21) Appl. No.: 11/524,864

(22) Filed: Sep. 21, 2006

(65) Prior Publication Data

US 2008/0077056 A1    Mar. 27, 2008

(51) Int. Cl.
*A61N 7/00* (2006.01)
(52) U.S. Cl. .......................................................... 601/3
(58) Field of Classification Search ................. 600/459, 600/439; 601/2–4; 606/27; 607/96
See application file for complete search history.

(56) References Cited

U.S. PATENT DOCUMENTS

| | | |
|---|---|---|
| 4,005,382 A | 1/1977 | Beaver |
| 4,074,564 A | 2/1978 | Anderson |
| 4,084,582 A | 4/1978 | Nigam |
| 4,161,121 A | 7/1979 | Zitelli et al. |
| 4,183,249 A | 1/1980 | Anderson |
| 4,207,901 A | 6/1980 | Nigam |
| 4,209,706 A | 6/1980 | Nunan |
| 4,223,560 A | 9/1980 | Glenn |
| 4,227,417 A | 10/1980 | Glenn |
| 4,231,373 A | 11/1980 | Waxman et al. |
| 4,241,412 A | 12/1980 | Swain |
| 4,241,610 A | 12/1980 | Anderson |
| 4,248,090 A | 2/1981 | Glenn |
| 4,257,271 A | 3/1981 | Glenn |
| 4,274,422 A | 6/1981 | Anderson et al. |
| 4,290,310 A | 9/1981 | Anderson |
| 4,317,370 A | 3/1982 | Glenn |
| 4,324,258 A | 4/1982 | Huebscher et al. |
| 4,325,381 A | 4/1982 | Glenn |
| 4,327,738 A | 5/1982 | Green et al. |

(Continued)

FOREIGN PATENT DOCUMENTS

CA    1332441    10/1994

(Continued)

OTHER PUBLICATIONS

R. Seip, et al., "Sonablate® 500: A Novel Platform for Transrectal Image-Guided HIFU Treatment of Localized Prostate Cancer," presented at the 32nd Annual Symposium of the *Ultrasonic Industry Association* (UIA), Oct. 2002, 28 pgs.

(Continued)

*Primary Examiner*—Eric F Winakur
*Assistant Examiner*—Lawrence N Laryea
(74) *Attorney, Agent, or Firm*—Reed Smith LLP; William J. McNichol, Jr.

(57) ABSTRACT

A HIFU system is disclosed including a fluid circulation system including a degasser.

10 Claims, 9 Drawing Sheets

U.S. PATENT DOCUMENTS

| | | |
|---|---|---|
| 4,341,120 A | 7/1982 | Anderson |
| 4,378,596 A | 3/1983 | Clark |
| 4,407,293 A | 10/1983 | Suarez, Jr. et al. |
| 4,410,826 A | 10/1983 | Waxman et al. |
| 4,413,630 A | 11/1983 | Anderson et al. |
| 4,449,199 A | 5/1984 | Daigle |
| 4,530,358 A | 7/1985 | Forssmann et al. |
| 4,586,512 A | 5/1986 | Do-huu et al. |
| 4,620,546 A | 11/1986 | Aida et al. |
| 4,638,436 A | 1/1987 | Badger et al. |
| 4,658,828 A | 4/1987 | Dory |
| 4,664,121 A | 5/1987 | Sanghvi et al. |
| 4,807,633 A | 2/1989 | Fry |
| 4,858,613 A | 8/1989 | Fry et al. |
| 4,917,096 A | 4/1990 | Englehart et al. |
| 4,945,898 A | 8/1990 | Pell et al. |
| 4,951,653 A | 8/1990 | Fry et al. |
| 4,955,365 A | 9/1990 | Fry et al. |
| 5,033,456 A | 7/1991 | Pell et al. |
| 5,036,855 A | 8/1991 | Fry et al. |
| 5,054,470 A | 10/1991 | Fry et al. |
| 5,058,416 A * | 10/1991 | Engelhardt et al. ......... 73/19.01 |
| 5,065,761 A | 11/1991 | Pell |
| 5,080,102 A | 1/1992 | Dory |
| 5,117,832 A | 6/1992 | Sanghvi et al. |
| 5,134,988 A | 8/1992 | Pell et al. |
| 5,149,319 A | 9/1992 | Unger |
| 5,195,509 A | 3/1993 | Rentschler et al. |
| 5,215,680 A | 6/1993 | D'Arrigo |
| 5,219,401 A | 6/1993 | Cathignol et al. |
| 5,247,935 A | 9/1993 | Cline et al. |
| 5,295,484 A | 3/1994 | Marcus et al. |
| 5,316,000 A | 5/1994 | Chapelon et al. |
| 5,391,197 A | 2/1995 | Burdette et al. |
| 5,409,002 A | 4/1995 | Pell |
| 5,409,006 A | 4/1995 | Buchholtz et al. |
| 5,443,069 A | 8/1995 | Schaetzle |
| 5,470,350 A | 11/1995 | Buchholtz et al. |
| 5,492,126 A | 2/1996 | Hennige et al. |
| 5,520,188 A | 5/1996 | Hennige et al. |
| 5,573,497 A | 11/1996 | Chapelon |
| 5,601,526 A | 2/1997 | Chapelon et al. |
| 5,620,479 A | 4/1997 | Diederich |
| 5,630,837 A | 5/1997 | Crowley |
| 5,643,179 A | 7/1997 | Fujimoto et al. |
| 5,676,692 A | 10/1997 | Sanghvi et al. |
| 5,722,411 A | 3/1998 | Suzuki et al. |
| 5,725,482 A | 3/1998 | Bishop |
| 5,762,066 A | 6/1998 | Law et al. |
| 5,769,790 A | 6/1998 | Watkins et al. |
| 5,817,021 A | 10/1998 | Reichenberger |
| 5,840,031 A | 11/1998 | Crowley |
| 5,873,902 A | 2/1999 | Sanghvi et al. |
| 5,879,314 A | 3/1999 | Peterson et al. |
| 5,882,302 A | 3/1999 | Driscoll, Jr. et al. |
| 5,906,580 A | 5/1999 | Kline-Schoder et al. |
| 5,993,389 A | 11/1999 | Driscoll, Jr. et al. |
| 6,016,452 A | 1/2000 | Kasevich |
| 6,083,159 A | 7/2000 | Driscoll, Jr. et al. |
| 6,093,883 A | 7/2000 | Sanghvi et al. |
| 6,126,619 A * | 10/2000 | Peterson et al. ............... 601/2 |
| 6,217,530 B1 | 4/2001 | Martin et al. |
| 6,334,846 B1 | 1/2002 | Ishibashi et al. |
| 6,375,634 B1 | 4/2002 | Carroll |
| 6,425,867 B1 | 7/2002 | Vaezy et al. |
| 6,500,133 B2 | 12/2002 | Martin et al. |
| 6,575,956 B1 | 6/2003 | Brisken et al. |
| 6,618,620 B1 | 9/2003 | Freundlich et al. |
| 6,656,136 B1 | 12/2003 | Weng et al. |
| 6,666,835 B2 | 12/2003 | Martin et al. |
| 6,676,601 B1 | 1/2004 | Lacoste et al. |
| 6,685,639 B1 | 2/2004 | Wang et al. |
| 6,685,640 B1 | 2/2004 | Fry et al. |
| 6,716,184 B2 | 4/2004 | Vaezy et al. |
| 6,772,490 B2 | 8/2004 | Toda |
| 6,812,204 B1 | 11/2004 | McHale et al. |
| 6,846,290 B2 | 1/2005 | Lizzi et al. |
| 6,875,176 B2 | 4/2005 | Mourad et al. |
| 2001/0008758 A1 | 7/2001 | McHale et al. |
| 2001/0014780 A1 | 8/2001 | Martin et al. |
| 2002/0035361 A1 | 3/2002 | Houser et al. |
| 2002/0095087 A1 | 7/2002 | Mourad et al. |
| 2002/0102216 A1 | 8/2002 | Lanza et al. |
| 2002/0193785 A1 | 12/2002 | Naghavi et al. |
| 2003/0018358 A1 | 1/2003 | Saadat |
| 2003/0028111 A1 | 2/2003 | Vaezy et al. |
| 2003/0040698 A1 | 2/2003 | Makin et al. |
| 2003/0060736 A1 | 3/2003 | Martin et al. |
| 2003/0149360 A1 * | 8/2003 | Tardy et al. .................. 600/437 |
| 2003/0171700 A1 | 9/2003 | Martin et al. |
| 2003/0191396 A1 | 10/2003 | Sanghvi et al. |
| 2003/0204141 A1 | 10/2003 | Nock et al. |
| 2003/0229331 A1 | 12/2003 | Brisken et al. |
| 2004/0030227 A1 | 2/2004 | Littrup et al. |
| 2004/0030268 A1 | 2/2004 | Weng et al. |
| 2004/0039312 A1 | 2/2004 | Hillstead et al. |
| 2004/0059220 A1 | 3/2004 | Mourad et al. |
| 2004/0071664 A1 | 4/2004 | McHale et al. |
| 2004/0106870 A1 | 6/2004 | Mast |
| 2004/0106880 A1 | 6/2004 | Weng et al. |
| 2004/0133192 A1 | 7/2004 | Houser et al. |
| 2004/0167403 A1 | 8/2004 | Nightingale et al. |
| 2004/0210289 A1 | 10/2004 | Wang et al. |
| 2004/0254419 A1 | 12/2004 | Wang et al. |
| 2004/0264293 A1 | 12/2004 | Laugharn, Jr. et al. |
| 2005/0015009 A1 | 1/2005 | Mourad et al. |
| 2005/0025797 A1 | 2/2005 | Wang et al. |
| 2005/0038340 A1 | 2/2005 | Vaezy et al. |
| 2005/0074407 A1 | 4/2005 | Smith |
| 2005/0154308 A1 | 7/2005 | Quistgaard et al. |
| 2005/0154309 A1 * | 7/2005 | Etchells et al. ............... 600/459 |
| 2005/0154431 A1 | 7/2005 | Quistgaard et al. |
| 2005/0193451 A1 | 9/2005 | Quistgaard et al. |
| 2006/0173344 A1 * | 8/2006 | Marian et al. ................ 600/459 |
| 2007/0010805 A1 * | 1/2007 | Fedewa et al. ............... 606/207 |
| 2007/0167825 A1 * | 7/2007 | Lee et al. ..................... 600/463 |
| 2007/0191711 A1 * | 8/2007 | Bush et al. ................... 600/437 |

FOREIGN PATENT DOCUMENTS

| | | |
|---|---|---|
| CA | 1338240 | 4/1996 |
| EP | 0596513 | 11/1994 |
| WO | WO 93/16641 | 9/1993 |
| WO | WO 97/47881 A1 | 12/1997 |
| WO | WO 98/58588 | 12/1998 |
| WO | WO 99/49788 | 10/1999 |
| WO | WO 01/28623 A2 | 4/2001 |
| WO | WO 01/28623 A3 | 4/2001 |
| WO | WO 01/82777 A2 | 11/2001 |
| WO | WO 01/82777 A3 | 11/2001 |
| WO | WO 01/82778 A2 | 11/2001 |
| WO | WO 02/24050 A2 | 3/2002 |
| WO | WO 2005/107601 A2 | 11/2005 |

OTHER PUBLICATIONS

T. Uchida, et al., "Clinical Outcome of High-Intensity Focused Ultrasound (HIFU) for the Treatment of Localized Prostate Cancer: 5-Years Experience", to appear in the *Proc. of the International Symposium on Therapeutic Ultrasonic*, 2004, 1 pg. (Abstract).

J.S. Tan, et al., "Design of Focused Ultrasound Phased Arrays for Prostate Treatment," IEEE Ultrasonics Symposium Proceedings, Puerto Rico, 2000, 5 pgs.

T. Gardner, et al., " HIFU Prostatectomy for Prostate Cancer: The USA Experience", to appear in the *Proc. of the International Symposium on Therapeutic Ultrasound*, 2004, 1 pg. (Abstract).

J. C. Rewcastle, Ph.D., "High Intensity Focused Ultrasound for Prostate Cancer: Clinical Results and Technical Evolution", Whitepaper, 2004, 14 pgs.

T. Uchida, et al., "Transrectal High-Intensity Focused Ultrasound for Treatment of Patients with Stage T1b-2N0M0 Localized Prostate Cancer: A Preliminary Report", *Japanese Journal of Endourology and ESWL*, vol. 16, 108-114, 2003.

T. Uchida, et al., "Transrectal High-Intensity Focused Ultrasound for Treatment of Patients with Stage T1b-2N0M0 Localized Prostate Cancer: A Preliminary Report", *Urology*, 2002, pp. 394-399.

T. Uchida, et al., "Transrectal High Intensity Focused Ultrasound for the Treatment of Localized Prostate Cancer," *International Symposium on Therapeutic Ultrasound*, 2002, 9 pgs.

S. Madersbacher, et al., "Effect of High-Intensity Focused Ultrasound on Human Prostate Cancer in Vivo", *Cancer Research* 55, Aug. 1995, pp. 3346-3351.

N. T. Sanghvi, et al., "Noninvasive Surgery of Prostate Tissue by High Intensity Focused Ultrasound: An Updated Report", *European Journal of Ultrasound*, vol. 9; 1999, pp. 19-29.

T. Uchida, et al., "Clinical Outcome of High-Intensity Focused Ultrasound for Treating Benign Prostate Hyperplasia: Preliminary Report", *Urology*, 1998, pp. 66-71.

L. D. Sullivan, et al., "Early Experience with High-Intensity Focused Ultrasound for the Treatment of Benign Prostatic Hypertropy", *British Journal of Urology*, 1997, pp. 172-176.

N. T. Sanghvi, et al., "Noninvasive Surgery of Prostate Tissue by High-Intensity Focused Ultrasound", *IEEE Transactions on Ultrasonics, Ferroelectrics, and Frequency Control*. vol. 43, No. 6, Nov. 1996, pp. 1099-1110.

S. Madersbacher, et al., "High-Intensity Focused Ultrasound in Urology", *Japanese Journal of Endourology and ESWL*, vol. 9, No. 1, 1996, pp. 5-15.

F. Fry, et al., "Ultrasound and Microbubbles: Their Generation, Detection and Potential Utilization in Tissue and Organ Therapy—Experimental", *Ultrasound in Medicine & Biology*, vol. 21, No. 9, 1995, pp. 1227-1237.

S. Madersbacher, et al., "Tissue Ablation in Benign Prostatic Hyperplasia with High Intensity Focused Ultrasound", *J. Urology*, vol. 152, Dec. 1994, pp. 1956-1961.

R. S. Foster, et al., "High-Intensity Focused Ultrasound for the Treatment of Benign Prostatic Hypertropy", *Seminars in Urology*, vol. XII, No. 3, pp. 200-204, Aug. 1994.

S. Umemura, et al., "Coagulation of Swine Live and Canine Prostate with a Prototype Split-Focus Transducer", *IEEE Ultrasonics Symposium*, 1999, 4 pgs.

J. Wu, et al., "Experimental Studies of Using a Split Beam Transducer for Prostate Cancer Therapy in Comparison to Single Beam Transducer", *IEEE Ultrasonics Symposium*, 1999, 4 pgs.

T. Uchida, "Localized Prostate Cancer Treatment with HIFU", Translated and updated from T*he Journal of Highly Advanced Medical Technology*, vol. 15 Mar. 2000, 1 pg.

R. Seip, et al., "Comparison of Split-Beam Transducer Geometries and Excitation Configurations for Transrectal Prostate HIFU Treatments", *IEEE Ultrasonics Symposium Proceedings*, 2001, 4 pgs.

R. Seip., "High-Intensity Focused Ultrasound (HIFU) Phased Arrays: Recent Developments in Transrectal Transducers and Driving Electronics Design," *Third International Symposium on Therapeutic Ultrasound*, Lyon, France, Jun. 2003, 6 pgs.

R. Seip, et al., "High-Intensity Focused Ultrasound (HIFU) Phased Arrays: Recent Developments in Transrectal Transducers and Driving Electronics Design," *Third International Symposium on Therapeutic Ultrasound*, Lyon, France, Jun. 2003 (Poster).

K. Ishida, et al., "Development and animal experiment of variable focusing HIFU system for prostate cancer treatment," *Proc. of the International Symposium on Therapeutic Ultrasound*, 2003, 6 pgs.

K. Ishida, et al., "Development and animal experiment of variable focusing HIFU system for prostate cancer treatment," *Proc. of the International Symposium on Therapeutic Ultrasound*, 2003, 18 pgs.

R. Seip, et al., "Annular and Cylindrical Phased Array Geometries for Transrectal High-Intensity Focused Ultrasound (HIFU) using PZT and Piezocomposite Materials," ISTU 4 Conference, Oct. 2004, Kyoto, Japan, 3 pgs.

R. Seip, et al., "High-Intensity Focused Ultrasound (HIFU) Multiple Lesion Imaging: Comparison of Detection Algorithms for Real-Time Treatment Control," *IEEE Ultrasonics Symposium Proceedings*, Munich, Germany, 2002, pp. 1395-1398.

R. Seip, et al., "Real-Time Detection of Multiple Lesions during High Intensity Focused Ultrasound (HIFU) Treatments," *International Symposium on Therapeutic Ultrasound*, 2002, 8 pgs.

N.T. Sanghvi, et al., "Decision Theory Applied to High-Intensity Focused Ultrasound (HIFU) Treatment Evaluation," 2003 AIUM Annual Meeting, Jun. 1-4, 2003, Montreal, Quebec, Canada, 24 pgs.

W. Chen, et al., "The Detection and Exclusion of Prostate Neuro-Vascular Bundle (NVB) in Automated HIFU Treatment Planning Using a Pulsed-Wave Doppler Ultrasound System," 2004 ISTU Conference, Kyoto, Japan, 3 pgs.

R. Seip, et al., "Transurethral High Intensity Focused Ultrasound: Catheter Based Prototypes and Experimental Results," *IEEE Ultrasonics Symposium Proceedings*, Puerto Rico, 2000, 4 pgs.

J. Tavakkoli, et al., "A Laparoscopic HIFU Probe for Kidney Ablation Prior to Partial Nephrectomy," *IEEE Ultrasonics Symposium Proceedings*, Atlanta, 2001, 4 pgs.

N.T. Sanghvi, et al., "Laparoscopically Delivered HIFU for Partial Renal Ablation," 17th International Congress on Acoustics, Sep. 2-7, 2001, Rome, Italy, 2 pgs.

J. Tavakkoli, et al., "Laparoscopic High Intensity Focused Ultrasound: Application to Kidney Ablation," *International Symposium on Therapeutic Ultrasound*, Seattle, 2002, 9 pgs.

J. Tavakkoli, et al., "A Laparoscopic HIFU Probe with Integrated Phased Array Ultrasound Imaging," *Third International Symposium on Therapeutic Ultrasound*, Jun. 2003, Lyon, France, 6 pgs.

J. Tavakkoli, et al., "A Laparoscopic HIFU Probe with Integrated Phased Array Ultrasound Imaging," *International Symposium on Therapeutic Ultrasound*, 2003 (Poster).

R. Seip, et al., "Automated HIFU Treatment Planning and Execution based on 3D Modeling of the Prostate, Urethra, and Rectal Wall", 2004 IEEE Ultrasonics Symposium Proceedings, 4 pgs.

R. Seip, et al., "Automated HIFU Treatment Planning and Execution based on 3D Modeling of the Prostate, Urethra, and Rectal Wall", 2004 IEEE Ultrasonics Symposium Proceedings (Poster).

J.S. Tan, et al., "Ultrasound Phased Arrays for Prostate Treatment", *J. Acoust. Soc. Am.*, vol. 109, No. 6, Jun. 2001, pp. 3055-3064.

R. Seip, et al., "Feasibility Study for the Treatment of Brachytherapy Failure Prostate Cancer using High-Intensity Focused Ultrasound, "*Third International Symposim on Therapeutic Ultrasound*, Lyon, France, Jun. 2003, 6 pgs.

M. Bailey, et al., "Caviation Detection and Suppression in HIFU," *Proc. of the International Symposium on Therapeutic Ultrasound*, 2003, 1 pg. (Poster).

The American Society for Therapeutic Radiology and Oncology Consensus Panel, "Consensus Statement: Guidelines for PSA Following Radiation Therapy," Int. J. Radiation Oncology Biol. Phys., vol. 37, No. 5, 1997, pp. 1035-1041.

N.T. Sanghvi, et al., "Total Prostate Ablation for the Treatment of Localized Prostate Cancer Using Image Guilded HIFU," presented at the 2002 IEEE Ultrasonics Symposium. (Poster).

J. C. Rewcastle, Ph.D., "High Intensity Focused Ultrasound for Prostate Cancer: 2006 Technology and Outcome Update", Whitepaper, 2006, 14 pgs.

Marcor Purification, FiberFlo® Oxygen Degas Capsule Filter, undated, 1 page.

HIFU Technology Pte. Ltd., The Haifu Knife Model-JC Focused Ultrasound Tumor Therapeutic System, undated, 1 page.

\* cited by examiner

HIFU PROBE FOR TREATING TISSUE WITH IN-LINE DEGASSING OF FLUID

FIELD OF THE INVENTION

The present invention relates to an apparatus and related method for the treatment of tissue, and in particular, for the non-invasive treatment of diseased tissue.

BACKGROUND AND SUMMARY OF THE INVENTION

Several techniques have been used in the past for the treatment of tissue including diseased tissue, such as cancer, to remove, destroy, or otherwise minimize the growth of the diseased tissue. For example, traditional methods of treating diseased prostate tissue include high intensity focused ultrasound ("HIFU"), radiation, surgery, Brachytherapy, cryoablation, hormonal therapy, and chemotherapy. Described herein are improved apparatus and method for treating tissue with high intensity focused ultrasound.

The treatment of tissue with HIFU is known. There are, for example, the techniques and apparatus described in U.S. Pat. Nos. 4,084,582; 4,207,901; 4,223,560; 4,227,417; 4,248,090; 4,257,271; 4,317,370; 4,325,381; 4,586,512; 4,620,546; 4,658,828; 4,664,121; 4,858,613; 4,951,653; 4,955,365; 5,036,855; 5,054,470; 5,080,102; 5,117,832; 5,149,319; 5,215,680; 5,219,401; 5,247,935; 5,295,484; 5,316,000; 5,391,197; 5,409,006; 5,443,069; 5,470,350; 5,492,126; 5,573,497; 5,601,526; 5,620,479; 5,630,837; 5,643,179; 5,676,692; 5,762,066; and 5,840,031. The disclosures of these references are hereby incorporated herein by reference.

Although the techniques, methods, and apparatus discussed herein have applicability to the treatment of tissue in general, this discussion will focus primarily on the treatment of prostate tissue including Benign Prostatic Hyperplasia (BPH) and prostatic cancer. However, the disclosed apparatus and methods may find applications in localization and treatment of a wide range of diseases which manifest themselves in a localized or "focal" manner, including cancers of the breast, brain, liver, and kidney. As explained herein, the disclosed apparatus uses a transrectal probe, but may be used with other types of probes including a transesophageal, laparoscopic or transvaginal probe.

As used herein the term "HIFU Therapy" is defined as the provision of high intensity focused ultrasound to a portion of tissue at or proximate to a focus of a transducer. It should be understood that the transducer may have multiple foci and that HIFU Therapy is not limited to a single focus transducer, a single transducer type, or a single ultrasound frequency. As used herein the term "HIFU Treatment" is defined as the collection of one or more HIFU Therapies. A HIFU Treatment may be all of the HIFU Therapies administered or to be administered, or it may be a subset of the HIFU Therapies administered or to be administered. As used herein the term "HIFU System" is defined as a system that is at least capable of providing a HIFU Therapy.

A probe housing a transducer is used to position a transducer proximate to the prostate of the patient. HIFU therapy requires a coupling medium (typically water) to couple the HIFU energy generated by the transducer into the body. At high intensities, ultrasound energy can create cavitation bubbles in the coupling medium, which interfere with the propagation of the sound waves, reducing their intensity and defocusing the beam. Furthermore, the cavitation bubbles can coalesce into larger air bubbles and accumulate on surfaces (such as an acoustic membrane) located between the transducer and the target tissue, effectively blocking the propagation of ultrasound into the body, or creating an interface mismatch at which undesired energy will accumulate at undesired locations, such as at the rectal wall. To reduce the likelihood of these effects degassed water is used as the coupling medium. As stated in U.S. Pat. No. 5,762,066, an acceptable level of degassed water for HIFU Therapy is water having a dissolved oxygen level of less than 3 parts per million (ppm).

Traditionally, degassed water is used in HIFU Therapy that is degassed prior to the treatment by known methods, such as boiling and vacuum degassing using a Nold DeAerator (Geokon, Inc., Lebanon, N.H. 03766). This requires the procurement of degassed water in advance. The fluid pathway of the HIFU System is traditionally filled/primed with this degassed water prior to commencing a HIFU Treatment. Over time, however, this degassed water will slowly ingas, as air permeates back into the degassed water through the connecting tubes, the acoustic membrane, and other pathways. Furthermore, during the filling/priming of the fluid pathway, air bubbles may be introduced into the degassed water contributing to ingasing the water. Both result in an increase in the level of dissolved gases in the degassed water which increases the chances of creating cavitation in the water during HIFU Therapy, especially as the HIFU Treatment progresses.

In addition, small bubbles introduced into the fluid pathway of a HIFU System have traditionally been difficult to remove as the bubbles tend to adhere to inside surfaces that are not easily accessible during probe preparation steps, such as the inside of the probe tip and the inside of the chilling system. Typically, during probe preparation, these bubbles are coaxed/manipulated in such a way by probe shaking and probe tip tapping so that a pump which circulates the water eventually removes the bubbles from their current location (i.e. the probe tip) and the bubbles end up at the top of a water reservoir, at which point they are unable to flow back into the probe tip to interfere with the treatment, as the water reservoir acts as a bubble trap. However, if all the bubbles are not removed, some bubbles may end up again in the probe tip in front of the HIFU beam negatively interfering with the delivery of HIFU Therapy to the patient.

In an exemplary embodiment of the present invention, a HIFU System is provided having a fluid circulation system including a degasser.

In another exemplary embodiment of the present invention, an apparatus for treating tissue is provided. The apparatus comprising a probe and a fluid circulation system. The probe including a transducer which is positionable proximate to the tissue, the transducer being configured to emit ultrasound energy and to sense ultrasound energy, a positioning member coupled to the transducer and configured to position the transducer relative to the tissue, and a fluid inlet and a fluid outlet. Both the fluid inlet and the fluid outlet being in fluid communication with a fluid pathway including an area adjacent a face of the transducer. The fluid circulation system being in fluid communication with the fluid inlet and the fluid outlet of the probe. The fluid circulation system including a pump configured to circulate a fluid throughout the fluid circulation system and the fluid pathway of the probe; a chiller configured to reduce a temperature of the fluid; a degasser which is configured to remove dissolved gases from the fluid; and a fluid adjustment member including a fluid reservoir. The fluid adjustment member being configured to both add additional fluid to the fluid circulation system and remove fluid from the fluid circulation system.

In a further exemplary embodiment of the present invention a method of preparing a HIFU system having a transrectal probe to provide treatment to the prostrate area of a patient is provided. The transrectal probe including a fluid pathway which includes an area a face of a therapy transducer. The method comprising the steps of: providing a fluid circulation system in fluid communication with the fluid pathway of the transrectal probe, the fluid circulation system including a pump configured to circulate a fluid through the fluid circulation system and the fluid pathway of the transrectal probe and a degasser which is configured to remove dissolved gases from the fluid passing through the degasser, the degasser including a vacuum pump; and electrically coupling the vacuum pump and the pump together such that each receives electrical power at generally the same time.

In yet another exemplary embodiment of the present invention, an apparatus for treating the prostrate from a position in a rectum of a patient is provided. The apparatus comprising a transrectal probe including an expandable acoustic membrane covering at least a portion of the probe and a transducer positioned behind the expandable acoustic membrane. The transducer being configured to emit ultrasound energy and to sense ultrasound energy. The apparatus further comprising a controller operably coupled to the transducer. The controller being configured to operate the transducer in an imaging mode wherein at least one image of the tissue is obtained from ultrasound energy sensed by the transducer and in a therapy mode wherein a plurality of treatment sites are treated with a HIFU Therapy with the transducer. The apparatus further comprising a fluid circulation system in fluid communication with a fluid pathway including an area adjacent a face of the transducer between the transducer and the acoustic membrane. The fluid circulation system including a pump configured to circulate a fluid throughout the fluid circulation system and the fluid pathway of the probe; a chiller configured to reduce a temperature of the fluid; a degasser configured to remove dissolved gases from the fluid, the degasser including a vacuum pump; and a fluid adjustment member including a fluid reservoir. The fluid adjustment member being configured to both remove fluid from the fluid circulation system and to add additional fluid to the fluid circulation system, wherein a first portion of the additional fluid is to be introduced to the fluid to expand the expandable acoustic membrane to contact the rectum of the patient when the probe is positioned in the rectum of the patient and a second portion of the additional fluid is to be introduced into the fluid to further expand the expandable acoustic membrane to position the transducer relative to the prostrate of the patient in a direction generally transverse to a longitudinal axis of the transrectal probe.

Additional features of the present invention will become apparent to those skilled in the art upon consideration of the following detailed description of the illustrative embodiments exemplifying the best mode of carrying out the invention as presently perceived.

BRIEF DESCRIPTION OF THE DRAWINGS

The detailed description of the drawings particularly refers to the accompanying figures in which.

DETAILED DESCRIPTION OF THE DRAWINGS

Figure 1:
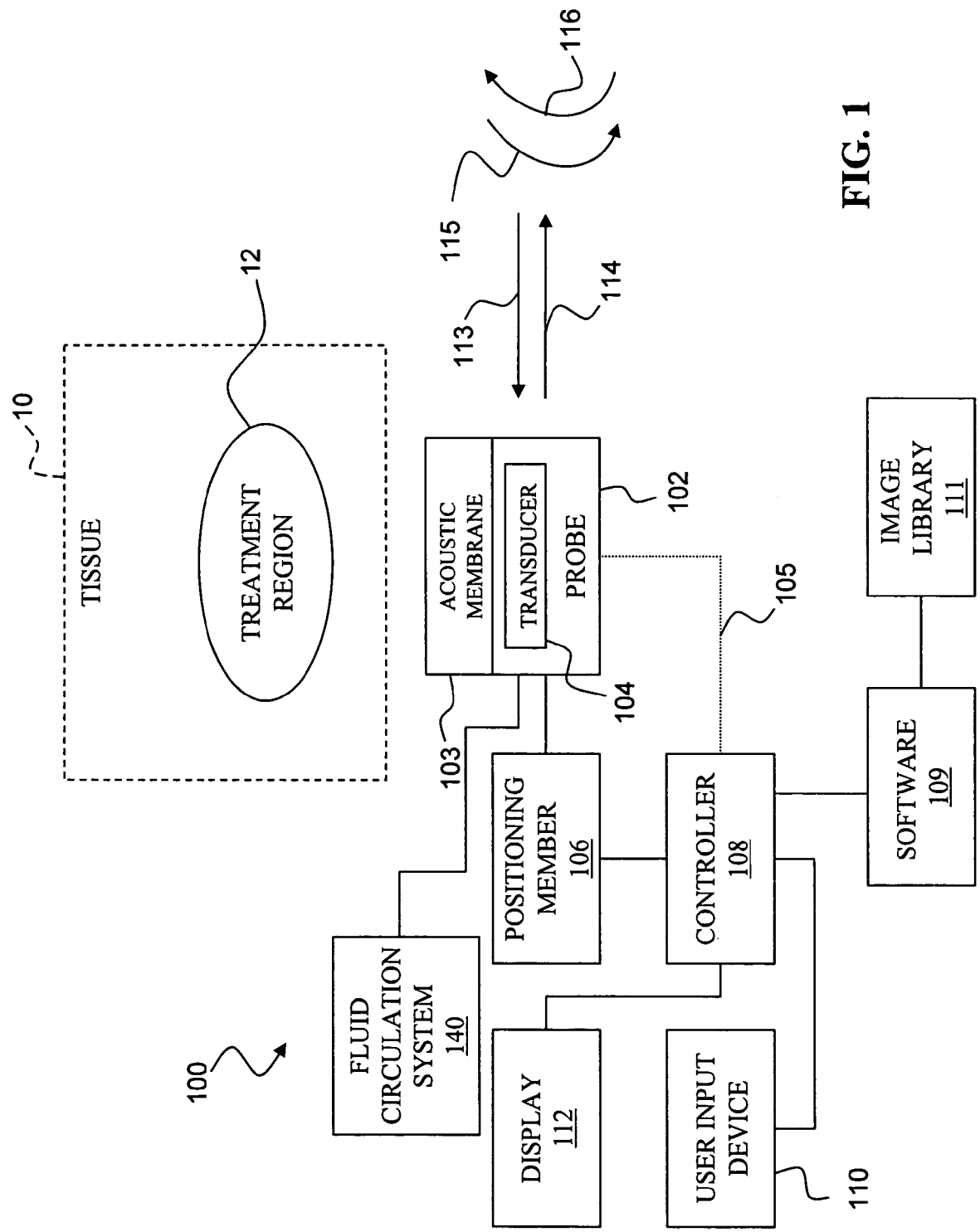
FIG. 1 is schematic view of an exemplary HIFU System of the present invention, the HIFU System being capable of imaging the tissue of the patient and to provide HIFU Therapy to at least a portion of the tissue at or proximate to a focus of a transducer of the HIFU System.

An exemplary HIFU System 100 is shown in FIG. 1. HIFU System 100 includes a probe 102 having a transducer member 104, a positioning member 106, a controller 108 operably coupled to probe 102 and the positioning member 106, a user input device 110 (such as keyboard, trackball, mouse, and/or touch screen), and a display 112. Probe 102 is operably connected to controller 108 through positioning member 106. However, as indicated by line 105 probe 102 may be directly connected with controller 108. Positioning member 106 is configured to linearly position transducer member 104 along directions 113, 114 and to angularly position transducer member 104 in directions 115, 116.

Transducer member 104 is positioned generally proximate to a region of tissue 10. In the case of the prostate, transducer 104 is positioned generally proximate to the prostate by the transrectal insertion of probe 102. Transducer member 104 is moved by positioning member 106 and controlled by controller 108 to provide imaging of at least a portion of tissue 10 including at least one treatment region 12 and to provide HIFU Therapy to portions of the tissue within at least one treatment region 12. As such, HIFU System 100 may operate in an imaging mode wherein at least a portion of tissue 10 may be imaged and in a therapy mode wherein HIFU Therapy is provided to portions of tissue 10 within at least one treatment region. As stated herein, treatment region 12 is defined as one or more portions of tissue which are to be treated during a HIFU Treatment. Treatment region 12 is illustratively shown as a continuous region. However, a treatment region might involve two or more distinct regions. Exemplary operation of an exemplary HIFU System in both an imaging mode and a therapy mode are discussed in U.S. patent application Ser. No. 11/177,827, filed Jul. 8, 2005, titled "METHOD AND APPARATUS FOR TREATMENT OF TISSUE", the disclosures of which are expressly incorporated by reference herein.

In one embodiment, controller 108 is configured to execute one or more programs provided as a portion of software 109 in the imaging mode and the therapy mode.

In one embodiment, transducer member 104 is a single crystal two element transducer. An exemplary transducer is disclosed in U.S. Pat. No. 5,117,832, the disclosure of which is expressly incorporated herein by reference. In a preferred embodiment, transducer 104 is capable of providing imaging of at least a portion of tissue 10 and of providing HIFU Therapy to at least a portion of tissue 10 within treatment region 12.

However, the present invention is not limited to the type of transducer implemented. On the contrary, various transducer geometries having a single focus or multiple foci and associated controls may be used including transducers which are phased arrays, such as the transducers disclosed in pending U.S. patent application Ser. No. 11/070,371, filed Mar. 2, 2005, titled "Ultrasound Phased Arrays," the disclosure of which is expressly incorporated herein by reference. Additional exemplary transducers and associated controls are disclosed in U.S. Pat. No. 5,762,066 and the additional patents and pending applications listed herein, the disclosures each of which are expressly incorporated herein by reference.

In one embodiment, a portion of probe 102 is covered by an acoustic membrane 103. Acoustic membrane 103 is an expandable membrane whose overall size is increased by placing a fluid on an interior of acoustic membrane 103. In one embodiment, the fluid is water or a generally acoustic transparent material and is provided by a reservoir or a chiller. The fluid may be used to remove heat from proximate to transducer 104 as well as expanding acoustic membrane 103.

Figure 2:
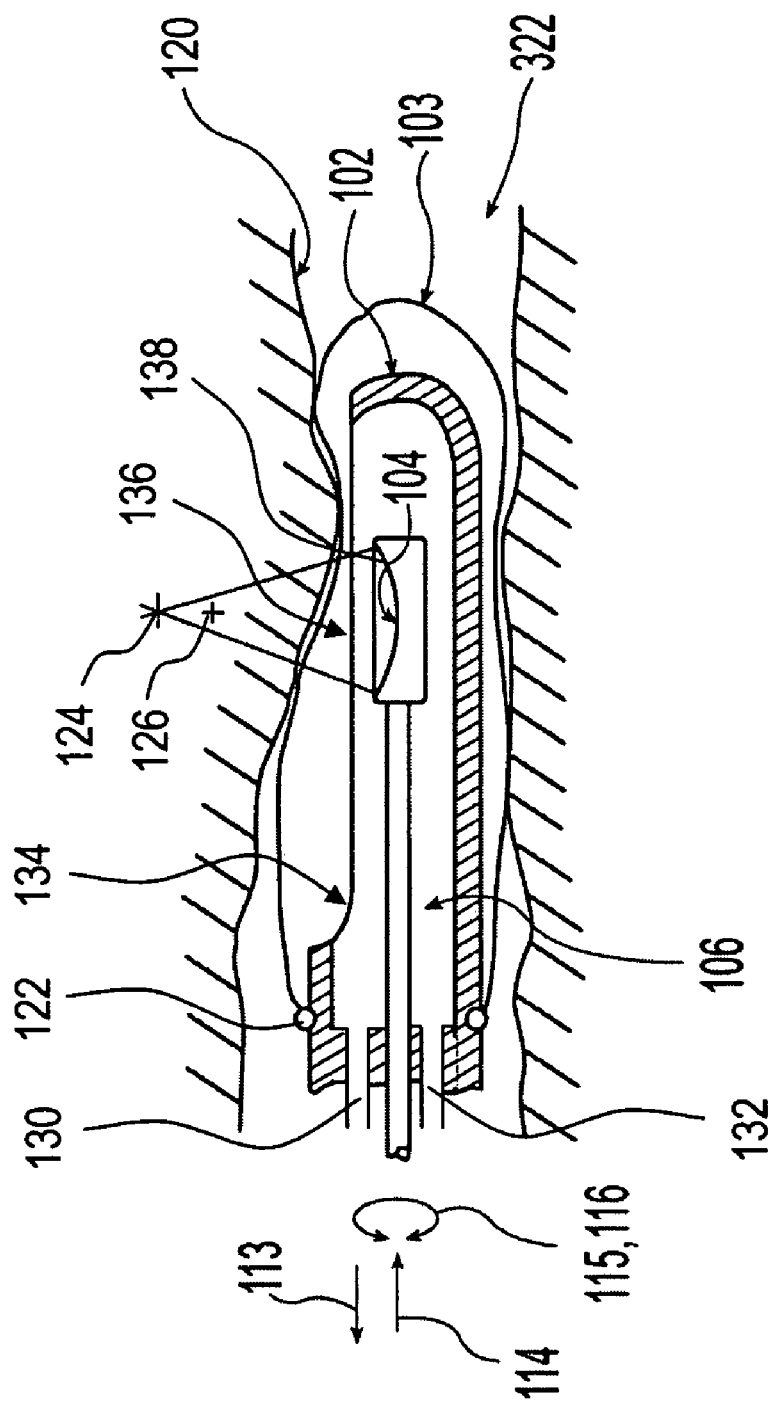
FIG. 2 is an exemplary view of a probe of the HIFU System of FIG. 1 positioned within the rectum of a patient.

Referring to FIG. 2, in one embodiment, acoustic membrane 103 is expanded such that it contacts or generally is adjacent to the surrounding tissue, such as rectal wall 120. In one embodiment, acoustic membrane 103 is a condom placed over a tip of probe 102, sealed with o-rings 122, and filled with water. Exemplary acoustic membranes and details of their operation in relation to respective other portions of exemplary HIFU Systems are provided in U.S. Pat. Nos. 5,762,066, 5,993,389, U.S. patent application Ser. No. 11/444,986, filed Jun. 1, 2006, titled LAPAROSCOPIC HIFU PROBE, and U.S. patent application Ser. No. 11/445,004, filed Jun. 1, 2006, titled LAPAROSCOPIC HIFU PROBE, the disclosures each of which are expressly incorporated by reference herein.

As shown in FIG. 2, probe 102 includes a fluid inlet 130 and a fluid outlet 132 which are in fluid communication with a fluid pathway 134. As explained herein degassed fluid from a fluid circulation system 140 of HIFU System 100 enters fluid inlet 130, passes through at least a portion of fluid pathway 134 and exits fluid outlet 132. Fluid pathway includes an area 136 adjacent a face 138 of transducer 104 between face 138 and acoustic member 103.

As explained in more detail herein additional fluid may be added to fluid circulation system 140 or the pressure of the fluid in fluid circulation system otherwise increased to cause acoustic membrane 103 to expand relative to its shape in FIG. 2 resulting in acoustic membrane 103 compressing against rectal wall 120. Further, more fluid may be added to fluid circulation system 140 or the pressure of the fluid in fluid circulation system 140 otherwise further increased to cause acoustic membrane 103 further expand and if effect move transducer 104 further away from rectal wall 120. This results in transducer 104 having its focus at a location 126 instead of location 124.

As stated herein, HIFU System 100 further includes fluid circulation system 140. Fluid circulation system 140 is configured provide a coupling fluid, such as degassed water, to fluid pathway 134 of probe 102. In one embodiment, fluid circulation system 140 continuously degasses the water passing there through using an inline degasser, in order to minimize or eliminate cavitation during HIFU Therapy.

Figure 3:
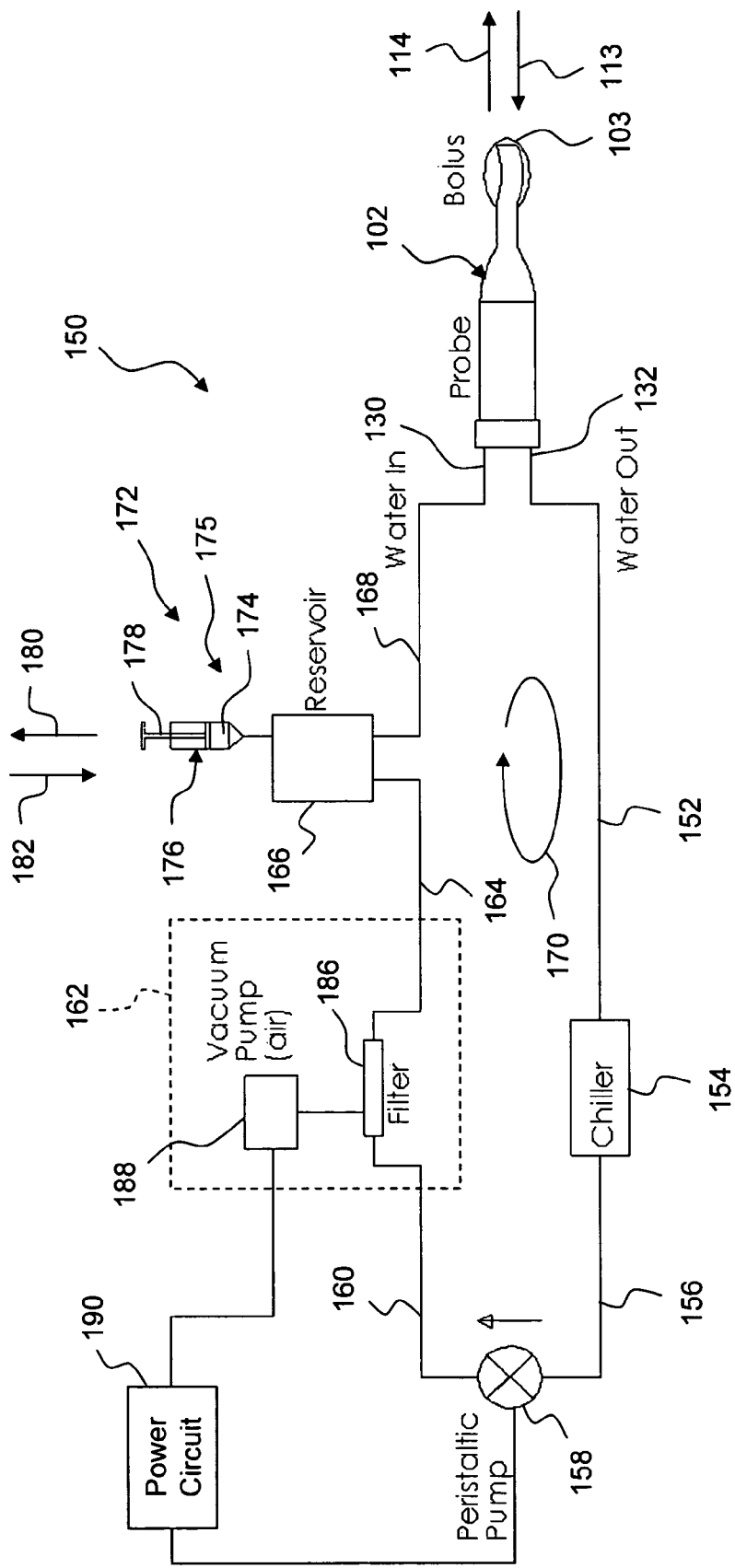
FIG. 3 is a diagrammatic view of an exemplary fluid circulation system of the HIFU System of FIG. 1.

Referring to FIG. 3, a first exemplary fluid circulation system 150 is shown which may be used for fluid circulation system 140 and which is capable of continuously degassing the coupling fluid. Fluid circulation system 150 includes a fluid conduit 152 in fluid communication with fluid outlet 132 of probe 102 and a chiller 154. Chiller 154 removes heat from the coupling fluid to chill the coupling fluid. By chilling the coupling fluid, the rectal wall 120 of the patient and the transducer 104 are chilled. This assists in reducing potential damage to rectal wall 120 and transducer 104. An exemplary chiller is Model No. LA-160-24-02 available from Supercool US Inc.—located at 819 A Street, San Rafael, Calif. 94901.

Fluid circulation system 150 further includes a fluid conduit 156 also in fluid communication with chiller 154 and in fluid communication with a peristaltic pump 158. Peristaltic pump 158 pumps the coupling fluid around fluid circuit 170 comprised of fluid circulation system 140 and the fluid pathway 134 of probe 102. An exemplary peristaltic pump is Model No. 313FDC/D available from Watson-Marlow Bredel—located at 37 Upton Technology Park, Wilmington, Mass. 01887.

Fluid circulation system 150 further includes a fluid conduit 160 also in fluid communication with peristaltic pump 158 and in fluid communication with a degasser 162. Degasser 162, as explained herein, removes dissolved gases from the fluid circulating in fluid circuit 170. Fluid circulation system 150 further includes a fluid conduit 164 also in fluid communication with degasser 162 and in fluid communication with a fluid reservoir 166. Fluid reservoir 166 contains a body of fluid that is circulated in fluid circuit 170. Fluid reservoir acts as a bubble trap, provides an easy means of filling/priming the fluid path, and increases the thermal capacity of the overall fluid path. Fluid circulation system 150 further includes a fluid conduit 168 also in fluid communication with reservoir 166 and in fluid communication with fluid inlet 130 of probe 102.

As shown in FIG. 2, fluid circulation system 150 further includes a fluid adjustment member 172 which includes a fluid reservoir 174. Illustratively, fluid adjustment member is shown as a syringe 175 having a body portion 176 and a plunger portion 178. By moving plunger portion 178 in direction 180 fluid is removed from fluid circuit 170 which results in acoustic membrane 103 being reduced in size or the pressure in fluid circuit 170 to drop. By moving plunger portion 178 in direction 182 additional fluid is added to fluid circuit 170 which results in acoustic membrane 103 expanding in size.

As stated herein, the expansion of acoustic membrane 103 may serve two purposes. First, to compress rectal wall 120 and provide an improved coupling of HIFU energy into the treatment region. If air is present between acoustic membrane 103 and rectal wall 120, a significant portion of the HIFU energy is reflected as explained in U.S. patent application Ser. No. 11/177,827, filed Jul. 8, 2005, titled "METHOD AND APPARATUS FOR TREATMENT OF TISSUE", the disclosures of which are expressly incorporated by reference herein. Second, to position transducer 104 relative to the tissue, such that the HIFU Therapy is provided at the desired location. The expansion of the acoustic membrane 103 results in the position of transducer 104 to be altered in directions 180 and 182 which are transverse to the longitudinal axis of probe 102 along directions 113, 114, illustratively generally perpendicular.

Although the components of fluid circulation system 150 are shown in a first configuration in FIG. 3, it should be understood that the components may be positioned in other configurations. For example, chiller 154 may be located at any position along fluid circuit 170, such as between degasser 162 and reservoir 166. In the illustrated configuration, the components of fluid circulation system 150 are arranged in a series configuration.

Degasser 162 includes a filter 186 and a vacuum pump 188. Filter 186 includes a plurality of fluid passageways (not shown) which are in fluid communication with fluid conduit 160 and fluid conduit 164. Further, the fluid passageways are air permeable and surrounded by a closed chamber. In one embodiment, filter 186 is a cartridge. Vacuum pump 188 is in fluid communication with the closed chamber of filter 186 which surrounds the fluid passageways. Vacuum pump 188 reduces the pressure on the closed chamber resulting in dissolved gases in the fluid passing through the fluid passageways to be drawn through the air-permeable walls of the passageways and out of the fluid. This results in the fluid to be degassed over time. An exemplary filter is Model No. SV-C-030-P, available from Marcor Purification USA located at 4450 Township Line Road, Skippack, Pa. 19474-1429. An exemplary vacuum pump is Model No. UNMP850KNDC-B available from KNF Neuberger having United States headquarters located at Two Black Forest Road, Trenton, N.J. 08691-1810. In one embodiment, filter 186 permits a flow rate of at least approximately 250 ml/min through fluid circulating system 150.

In one embodiment, vacuum pump 188 and peristaltic pump 158 are coupled to the same power circuit 190. Power circuit 190 provides power to both of vacuum pump 188 and peristaltic pump 158 at the same time. As such, at any time that peristaltic pump 158 is circulating the coupling fluid in fluid circuit 170 vacuum pump 188 is degassing the coupling fluid. By continuously degassing the coupling fluid with degasser 162, a user may use a non-degassed coupling fluid, such as tap water or distilled water, for the coupling fluid without the risk of adversely affecting the HIFU Treatment assuming the user waits for a period of time sufficient to degas the coupling fluid to an acceptable level. In one example, wherein tap water or distilled water is the coupling fluid an acceptable level is up to about 3 ppm and the corresponding period of time is about fifteen minutes. In one embodiment, power circuit 190 includes a switch actuable by a user to activate power circuit 190.

Figure 4:
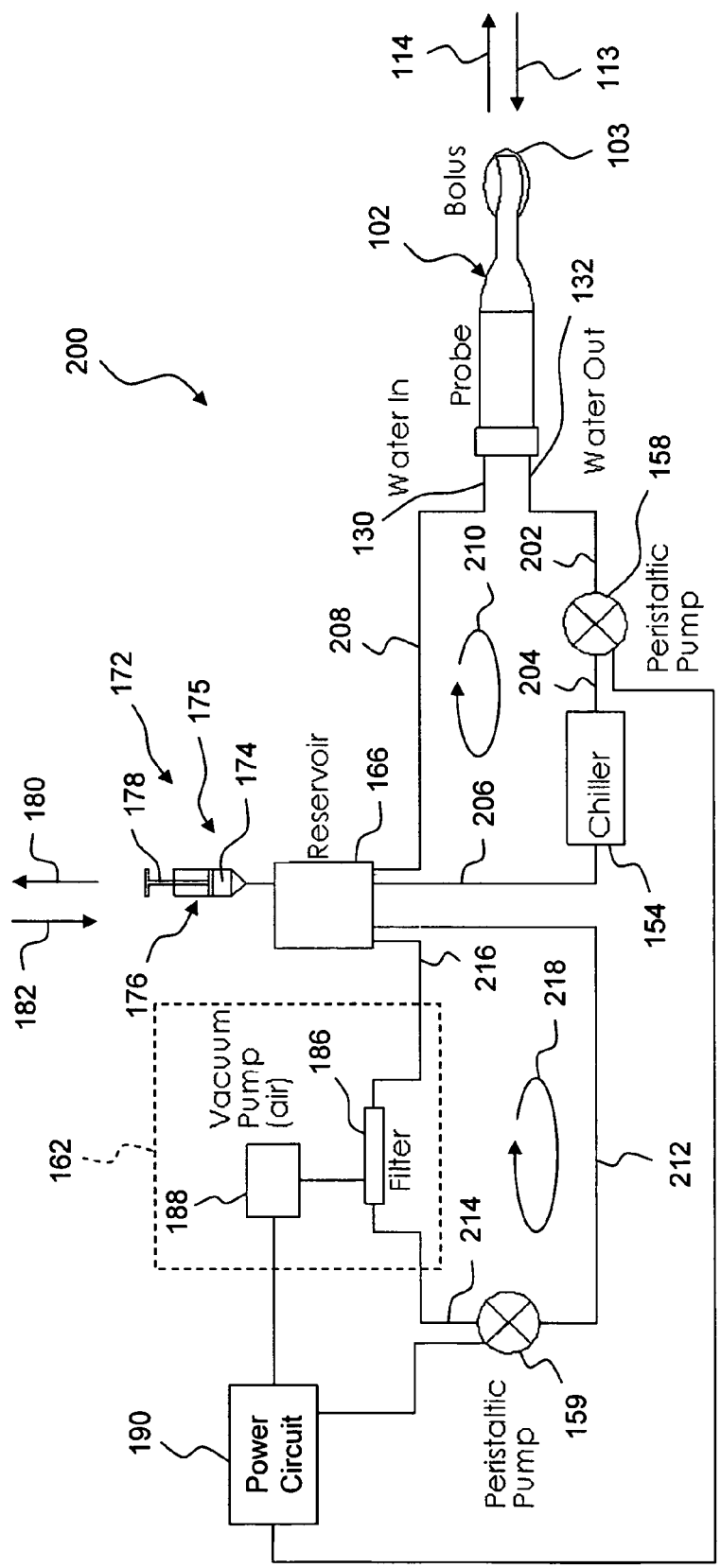
FIG. 4 is a diagrammatic view of another exemplary fluid circulation system of the HIFU System of FIG. 1.

Referring to FIG. 4, a second exemplary fluid circulation system 200 is shown which may be used for fluid circulation system 140. Fluid circulation system 200 includes many of the same components as fluid circulation system 150 as indicated by the use of the same reference numerals. Fluid circulation system 200 includes a fluid conduit 202 in fluid communication with fluid outlet 132 of probe 102 and with peristaltic pump 158 and a fluid conduit 204 in fluid communication with chiller 154 and in fluid communication with peristaltic pump 158.

Fluid circulation system 200 further includes a fluid conduit 206 in fluid communication with chiller 154 and reservoir 166 and a fluid conduit 208 in fluid communication with reservoir 166 and fluid inlet 130 of probe 102. Fluid conduits 202, 204, 206, and 208, chiller 154, peristaltic pump 158, reservoir 166 and the fluid pathway 134 of probe 102 form a first fluid circuit 210. Peristaltic pump 158 circulates the coupling fluid around first circuit 210.

Fluid circulation system 200 further includes a fluid conduit 212 in fluid communication with reservoir 166 and a second peristaltic pump 159. In one embodiment, pump 159 is generally identical to pump 158. Fluid circulation system 200 further includes a fluid conduit 214 in fluid communication with second peristaltic pump 159 and in fluid communication with degasser 162 and a fluid conduit 216 in fluid communication with degasser 162 and reservoir 166. Fluid conduits 212, 214, and 216, degasser 162, second peristaltic pump 159, and reservoir 166 form a second fluid circuit 218.

As shown in FIG. 4, first fluid circuit 210 and second fluid circuit 218 intersect at reservoir 166. As such, fluid may pass from first fluid circuit 210 into second fluid circuit 218 and may pass from second fluid circuit 218 into first fluid conduit 210. As shown in FIG. 4, first fluid circuit 210 provides the coupling fluid to probe 102 and second fluid circuit 218 degasses the coupling fluid. By placing degasser 162 in a parallel circuit with first circuit 210, fluid circulation system may use a filter 186 having a lower flow rate than fluid circulation system 150.

Although the components of fluid circulation system 200 are shown in a first configuration in FIG. 4, it should be understood that the components may be positioned in other configurations. For example, peristaltic pump 158 may be located at any position along fluid circuit 210, such as between chiller 154 and reservoir 166.

In one embodiment, vacuum pump 188 and peristaltic pumps 158 and 159 are coupled to the same power circuit 190. Power circuit 190 provides power to both of vacuum pump 188 and peristaltic pumps 158 and 159 at the same time. As such, at any time that peristaltic pumps 158 and 159 are circulating the coupling fluid in fluid circuits 210 and 218, vacuum pump 188 is degassing the coupling fluid. By continuously degassing the coupling fluid with degasser 162, a user may use a non-degassed coupling fluid, such as tap water or distilled water, for the coupling fluid without the risk of adversely affecting the HIFU Treatment assuming the user waits for a period of time sufficient to degas the coupling fluid to an acceptable level.

Fluid circulation system 150 has a high enough flow rate to provide adequate cooling to transducer 104 and/or rectal wall 120. In one embodiment, fluid circulation system 150 has a flow rate of about 250 ml/min which provides adequate cooling to transducer 104 and/or rectal wall 120. Fluid circulation system 200, in one embodiment, has a flow rate of about 250 ml/min in first fluid circuit 210 and a flow rate of about 250 ml/min or less in second fluid circuit 218.

In fluid circulation system 150 the coupling fluid passes degasser 162 each cycle prior to introducing the coupling fluid to probe 102. Although fluid circulation system 200 does not pass the coupling fluid through degasser 162 prior to introducing the coupling fluid to probe 102, the coupling fluid is effectively degassed because eventually the coupling fluid does pass into the second circuit 218 and pass through degasser 162 as it mixes in the reservoir 166.

Figure 5:
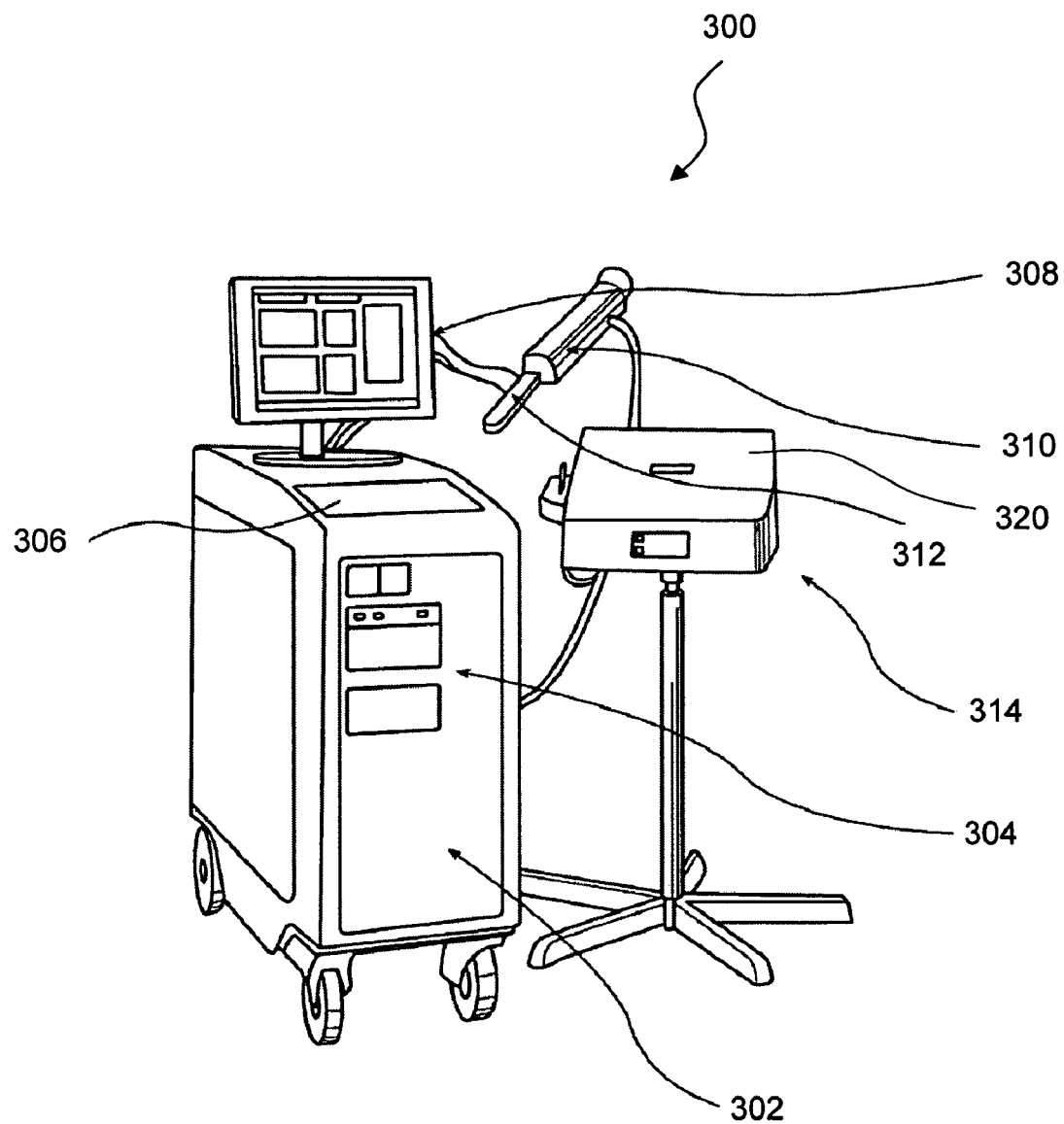
FIG. 5 is an exemplary embodiment of the HIFU System of FIG. 1.

Referring to FIG. 5, an exemplary HIFU System 300 is shown, the Sonablate® 500 HIFU System available from Focus Surgery, Inc., located at 3940 Pendleton Way, Indianapolis, Ind. 46226. HIFU System 300 includes a console 302 which houses or supports a controller (not shown), such as a processor and associated software; a printer 304 which provides hard copy images of tissue 10 and/or reports as described in more detail in U.S. patent application Ser. No. 11/177,827, filed Jul. 8, 2005, titled "METHOD AND APPARATUS FOR TREATMENT OF TISSUE", the disclosures of which are expressly incorporated by reference herein, a user input device 306 such as a keyboard, trackball, and/or mouse; and a display 308 for displaying images of tissue 10 and software options to a user, such as a color display. Further, shown is a probe 310 which includes a transducer member (not shown), and a positioning member (not shown). Also shown is an articulated probe arm 312 which is coupled to console 302. Articulated probe arm 312 orients and supports probe 310. A fluid circulation system 314 is also shown. Chiller 314, in one embodiment, provides a water path with a heat exchanger for the transducer member of probe 310 to actively remove heat from the transducer member during a HIFU Treatment.

Figure 6:
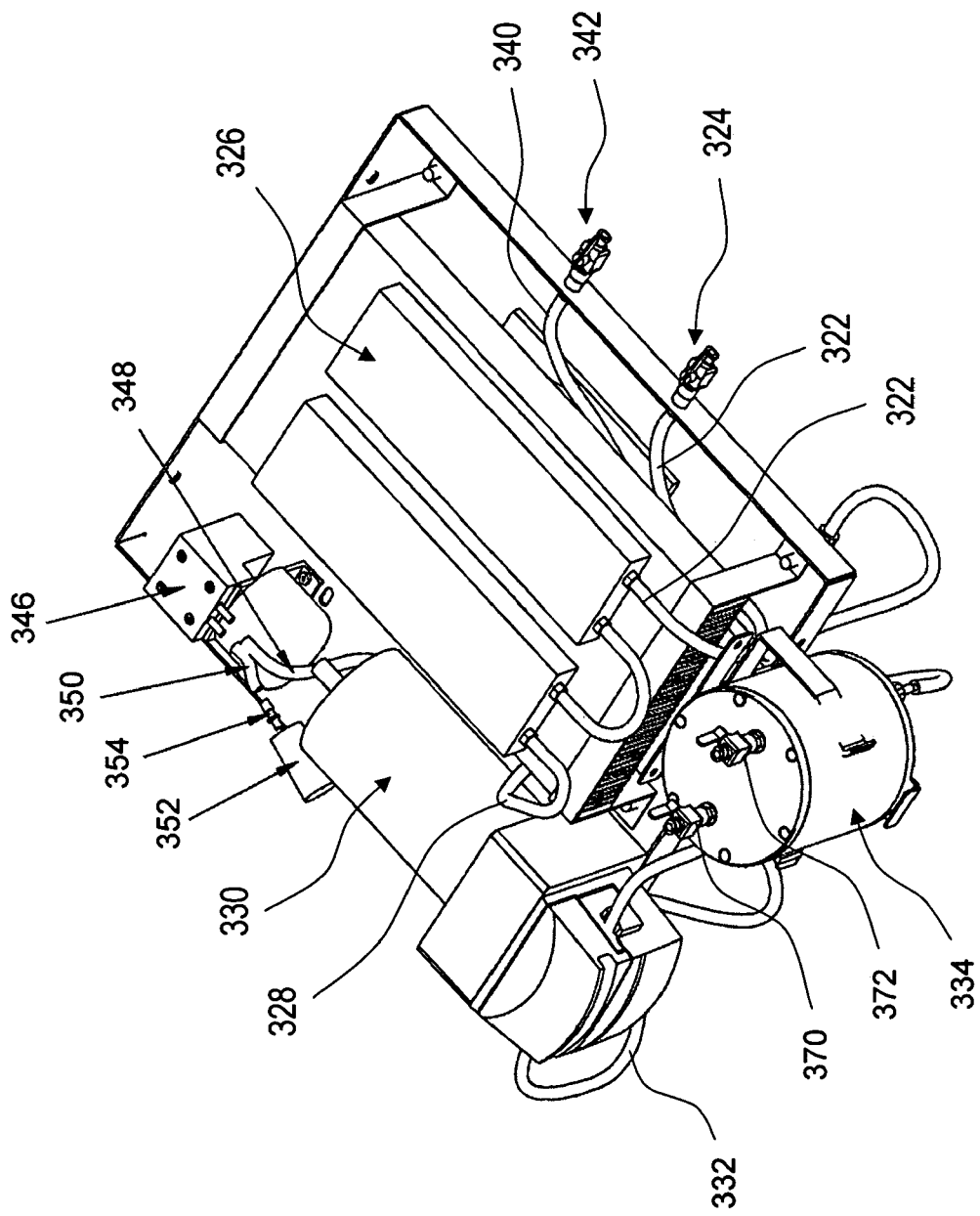
FIG. 6 is perspective view of a portion of the HIFU System of FIG. 5.
Figure 7:
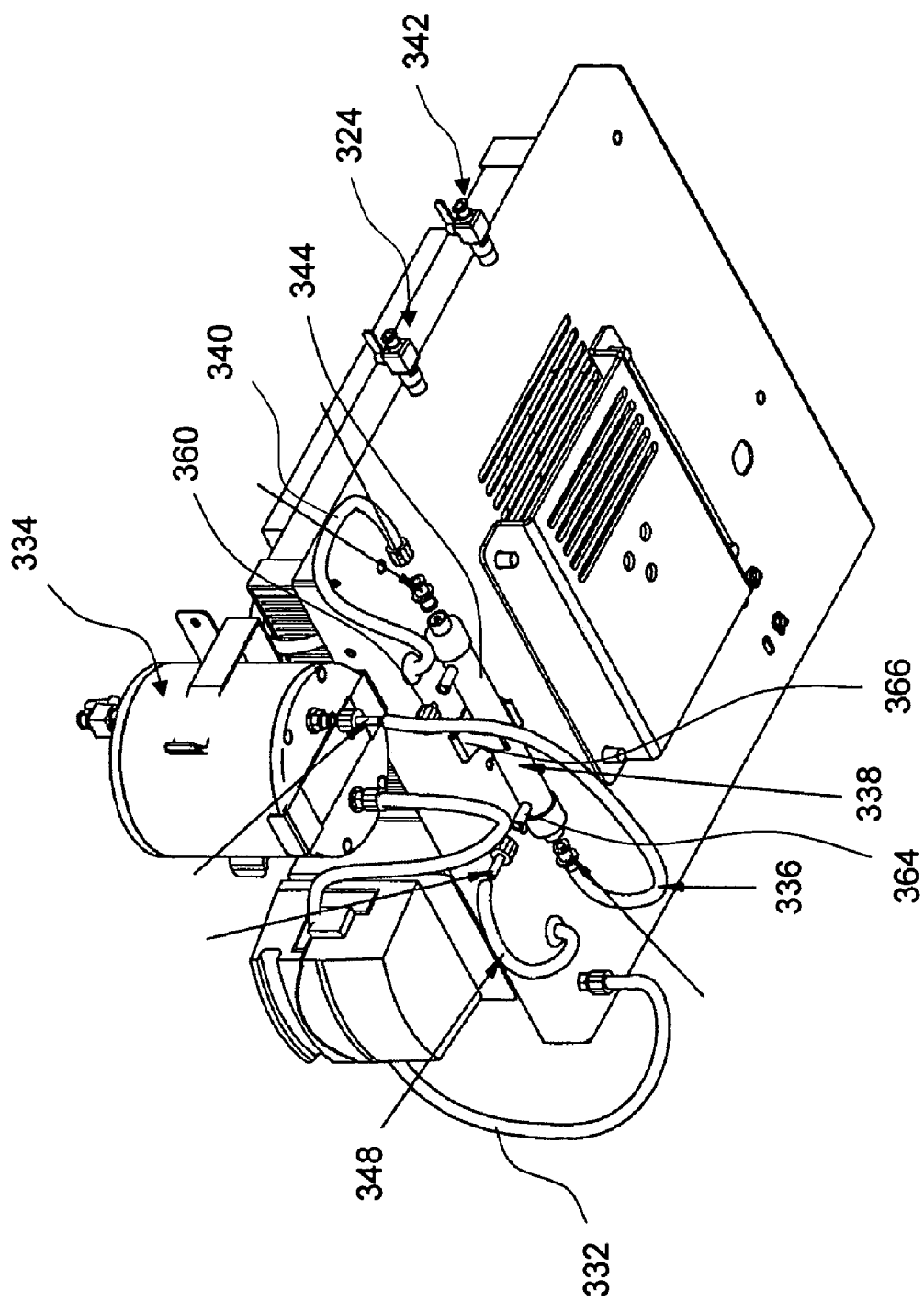
FIG. 7 is a perspective view of a portion of the HIFU System of FIG. 5.

HIFU System 300, in one embodiment, uses distilled and non-degassed water in the fluid circulation system 314 and the fluid pathway of probe 310. Fluid circulation system 314 operates to degas the water. Referring to FIGS. 6 and 7, fluid circulation system 314 is shown with a cover 320 removed. Fluid circulation system 314 is generally the same as fluid circulation system 150. A fluid conduit 322 (see FIG. 6), a section tygon ⅛ inch plastic tubing, is in fluid communication with a fitting 324 which is to be coupled to a fluid outlet of probe 310 and with a chiller unit 326. An exemplary chiller unit 326 is Model No. LA-160-24-02 available from Supercool US Inc. located at 819 A Street, San Rafael, Calif. 94901.

Chiller 326 is further in fluid communication with a fluid conduit 328 which is in fluid communication with a peristaltic pump 330. Peristaltic pump 330 is in fluid communication with a fluid conduit 332 which is in fluid communication with a reservoir 334. Reservoir 334 is further in fluid communication with a fluid conduit 336 which is in fluid communication with a filter cartridge 338 of a degasser. Fluid cartridge 338 is in fluid communication with a fluid conduit 340 which is in fluid communication with a fitting 342 which is to be coupled to a fluid inlet of probe 310.

Once probe 310 is connected to fluid circulation system 314 a coupling fluid, such as water, is pumped by pump 330 from reservoir 334 through fluid conduit 336, filter 338, and fluid conduit 340, on to probe 310, back to fluid conduit 322, through chiller 326, through fluid conduit 328 and pump 330, and finally through fluid conduit 332 back to reservoir 334. As such, the components of fluid circulation system 314 are connected together in series.

Filter cartridge 338 includes a plurality of fluid passageways each in fluid communication with fluid conduit 336 and fluid conduit 340. In addition, filter cartridge 338 includes a closed space bounded by housing 344 which surrounds the plurality of fluid passageways. The closed space is in fluid communication (air) with a vacuum pump 346 (see FIG. 6) through fluid conduit 348. Fluid conduit 348 is shown backed away from vacuum pump 346 to illustrate the connection ports of vacuum pump 346. Vacuum pump 346 reduces the pressure in the closed space resulting in dissolved gases in the coupling fluid being drawn through air-permeable membranes of the plurality of fluid passageways of filter cartridge 338 thereby lowering the amount of dissolved gas in the coupling fluid. An exemplary filter cartridge 338 is Model No. SV-C-030-P available from Marcor Purification USA located at 4450 Township Line Road, Skippack, Pa. 19474-1429 and an exemplary vacuum pump is Model No. UNMP850KNDC-B available from KNF Neuberger located at Two Black Forest Road, Trenton, N.J. 08691-1810. Vacuum pump 346 is in fluid communication (air) with a muffler 352 through a fluid conduit 350 and a fitting 354 to minimize operation noise.

In one embodiment, vacuum pump 346 and peristaltic pump 330 are coupled to the same power circuit so that each one is powered up at generally the same time. Further, this ensures that whenever pump 330 is operating, the degasser is degassing the coupling fluid.

In one embodiment, a user connects probe 310 to fluid circulation system 314 and fills/primes the fluid pathway with a coupling fluid. The coupling fluid is degassed by the degasser which includes filter cartridge 338 and vacuum pump 346. The inclusion of the degasser in fluid circulation system 314 enables the operator to degas the coupling fluid, such as water, during the system preparation steps and continuously during the treatment. This alleviates the need for the operator to procure degassed water for the operation of the system 314.

Figure 8:
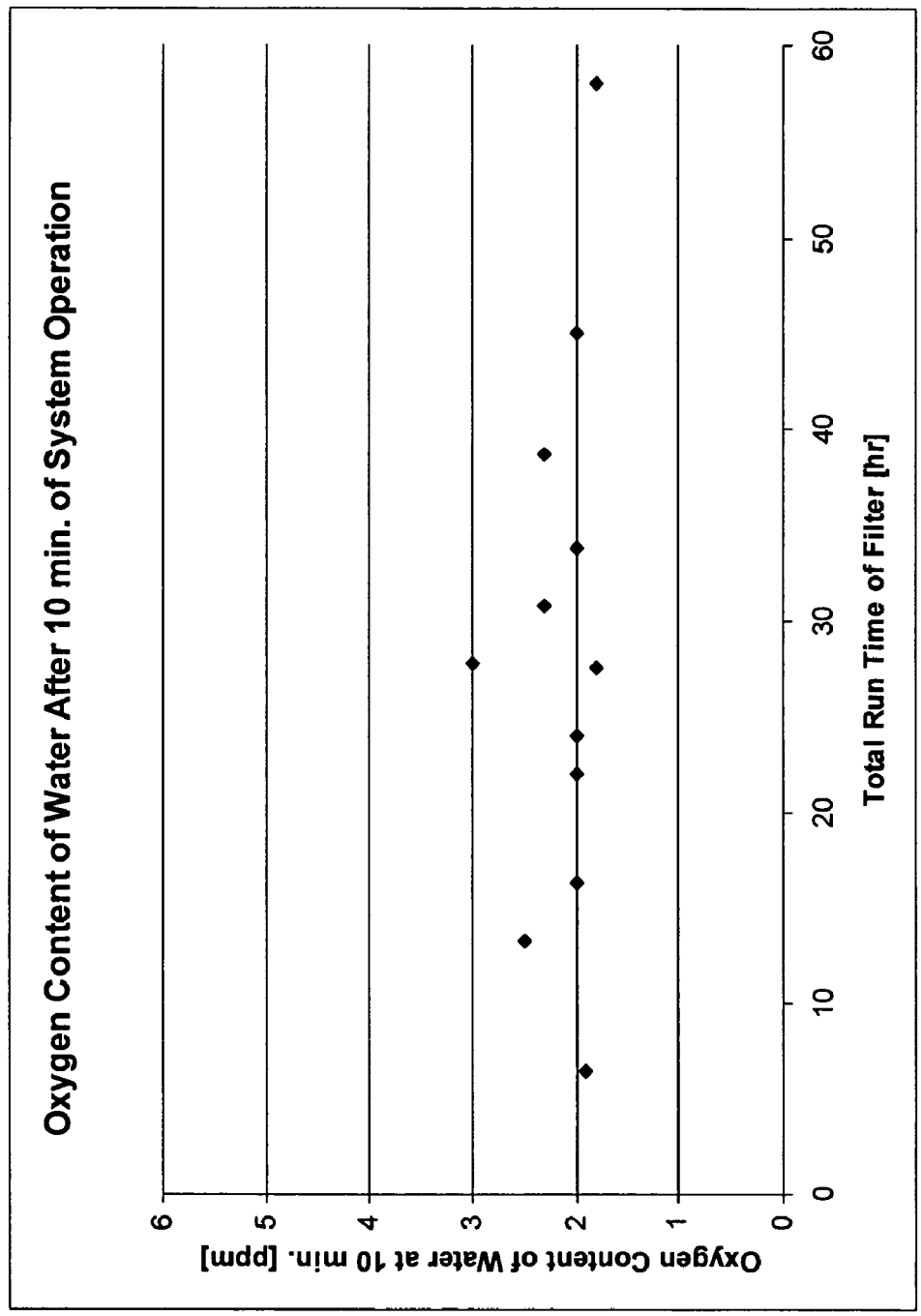
FIG. 8 is a graphical representation of the amount of dissolved oxygen present in the water of the fluid circulation system of the HIFU System of FIG. 5 after 10 minutes, showing no degassing performance degradation over time when the filter is re-used.
Figure 9:
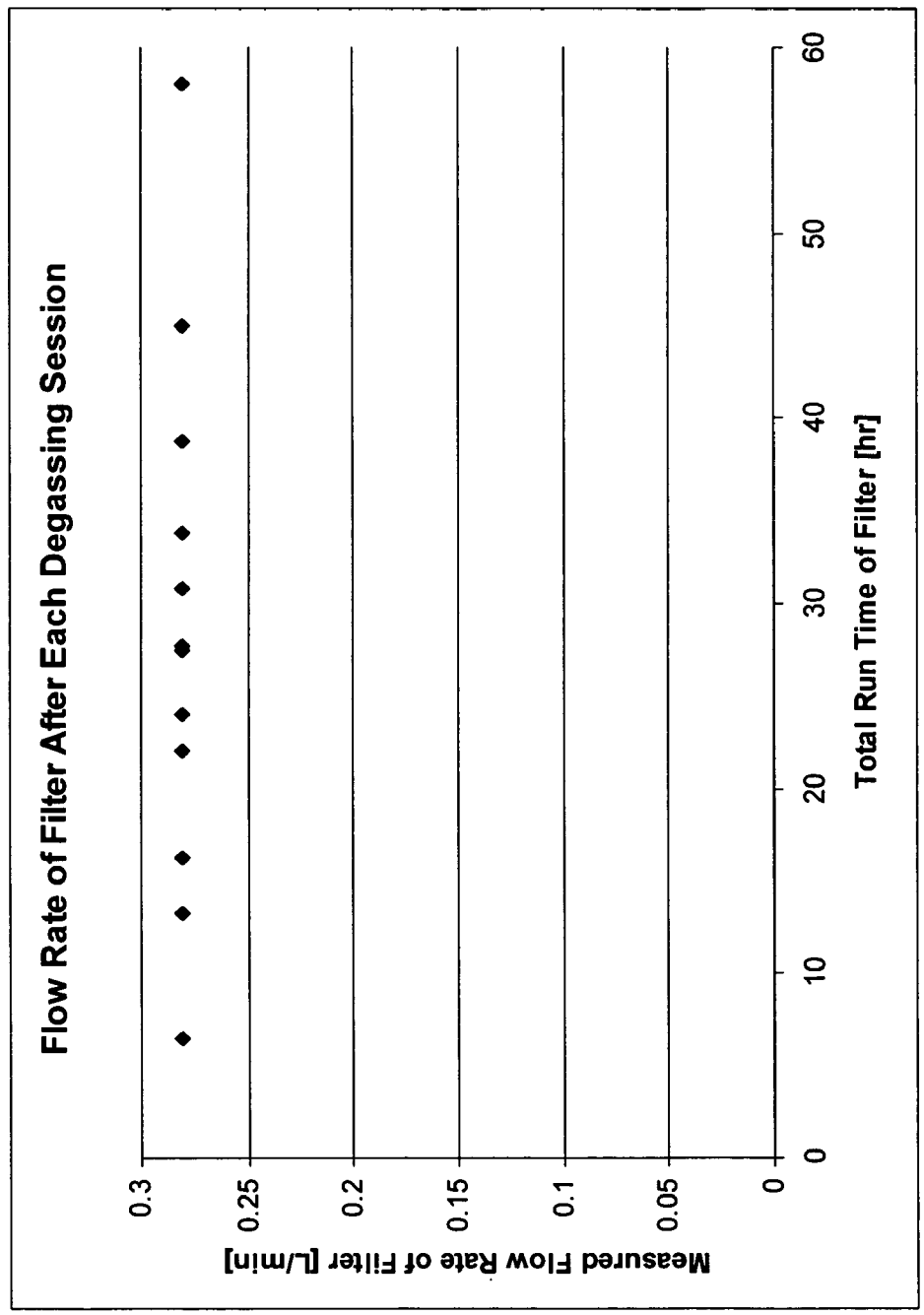
FIG. 9 is a graphical representation of the flow rate through a degasser of the fluid circulation system of the HIFU System of FIG. 5.

In one embodiment, fluid circulation system 314 is able to degas the entire water volume present in the probe/tubing/chiller/reservoir system from 7 ppm dissolved oxygen content (typical dissolved oxygen content of tap water) to less than 2 ppm dissolved oxygen content in approximately 15 minutes. In one example, the water that is present in the probe/tubing/chiller/reservoir system is degassed from 7-8 ppm down to approximately 3 ppm in less than 15 minutes (for 250 ml/min flow rate, vacuum of 22 in. of mercury, 450 ml starting water volume), and down to 1 ppm for the remainder of the HIFU treatment. Referring to FIG. 8, the oxygen content of the water flowing through fluid circulation system 314 is about 3 ppm or less after 10 minutes of operation, and no degassing performance degradation is visible even after having used the same filter for more than 60 hours. The final level of dissolved oxygen content in the coupling fluid is largely a function of the vacuum level. Applying a larger vacuum to the filter cartridge 338 results in faster degassing performance and lower levels of dissolved oxygen. Referring to FIG. 9, the flow rate of fluid circulation system 314 maintains relatively constant at about 275 ml/min, indicating that a filter cartridge may be re-used for many treatments without loosing degassing and cooling performance.

Referring to FIG. 7, fluid cartridge 338 includes another connection port 358 to the closed space that is capped with a cap 360. In one embodiment, fluid cartridge 338 is replaced in the following manner. First, a new filter cartridge 338 is removed from its packaging. One of the filter caps (similar to cap 360) is removed from port 364 located on the side of housing 344. Cap 360 should remain firmly attached. Fluid conduit 348 is connected to port 364. Fluid conduits 336 and 340 are connected to the end ports of filter cartridge 338 which are in fluid communication with the plurality of fluid passageways therein. All of the fluid connections should be checked to make sure they are tight and fluid cartridge 338 is then coupled to a clip 366 located on the bottom of the housing of the fluid circulation system 314. In one embodiment, a new filter cartridge 338 is used for each patient that is receiving a HIFU Treatment. In another embodiment, a simple vacuum gauge is connected to the second port of the filter cartridge, to offer visual feedback to the user of the vacuum applied by the vacuum pump, and thus an indication of the proper functioning of the system.

It should be noted that fittings 324 and 342 to and from probe 102 include valves such that fluid circulation system 314 may cutoff from probe 310. Further, reservoir 334 includes two fitting 370 and 372 to which a fluid supplying conduit may be attached or a fluid adjustment member, such as fluid adjustment member 172. Fittings 370 and 372 also include valves such that fittings 370 and 372 may be opened or closed.

In one embodiment, fluid circulation system 314 and probe 310 are setup as follows. A coupling fluid is provided to reservoir 334 of fluid circulation system 314 through one of fittings 370 and 372. A degassed coupling fluid is not required since the degasser will degas the coupling fluid. In addition, it should be verified that fittings 324 and 342 are open to permit fluid flow to and from probe 310. A fluid adjustment member 172, a syringe 175, is filled with a coupling fluid and attached to one of fittings 370 and 372. The coupling fluid in syringe 175 is completely emptied into reservoir 334 causing an acoustic membrane of probe 310 to expand. The fitting connection to syringe 175 is closed. Pump 330 and pump 346 are activated. In one example, pump 330 and pump 346 are activated by clicking a "Pump ON" button on HIFU System 300. The pump 330 and pump 346 should be run for a sufficient time period to degas the coupling fluid to an acceptable level for HIFU Therapy. In one example, the coupling fluid is degassed down to about 3 ppm in a time period of about fifteen minutes. The chiller 326 may also activate based on the temperature of the coupling fluid. Chiller 326 monitors the temperature of the coupling fluid and activates if the temperature is above a setpoint temperature. Pumps 330 and 346 are deactivated. In one example, pumps 330 and 346 are deactivated by clicking on the "Pump OFF" button on HIFU System 300. The fitting 370 and 372 that syringe 175 is connected to is opened and a first amount of fluid is removed from the reservoir 334 into fluid reservoir 174 of syringe 175. The fitting is again closed and the coupling fluid in fluid reservoir 174 is tested to see if the level of dissolved gases is below about 3 ppm. In one example, a CHEMets brand water test kit is used to test the level of dissolved gas in the coupling fluid. Assuming the level of dissolved gas is acceptable, syringe 175 is reattached to one of fittings 370 and 372 and an additional amount of coupling fluid is removed from reservoir 334 causing the acoustic membrane of probe 310 to get smaller readying probe 310 for insertion into the rectum of the patient. This procedure also ensures that the water needed for acoustic membrane or bolus expansion and probe positioning will also be degassed. In one example, about 50 ml of coupling fluid is moved into fluid reservoir 174 of syringe 175. Pumps 330 and 346 are again activated to continue to degas the water in the system prior to probe usage for HIFU Therapy.

If when tested the level of dissolved gas is not below 3 ppm it is likely that the degassing ability of the system has been compromised. The following should be verified: (1) that all connections are air-tight, and all tubing is correctly attached (tighten as needed); (2) that all tubing and the reservoir are clean (clean or replace, as needed); (3) that the filter cartridge is new and not defective (replace as needed); and (4) that the vacuum pump 346 produces a vacuum when pump 330 is activated (verify this by temporarily disconnecting the vacuum tube 348 from the filter cartridge 338 and noting suction at the tube connector), or using a vacuum gauge as described previously. If the problem persists, the degasser may be bypassed by attaching fluid conduit 340 to reservoir 334. If this option is chosen a degassed coupling fluid (<_3 ppm dissolved oxygen content) should be used.

In addition, fluid circulation system 314 may remove approximately 2 cubic centimeters of air (i.e. not dissolved in the water) from the system per hour. As such, over time any larger air bubbles in the system will be removed from the system without requiring probe tapping. As the water is degassed, air from the air bubbles will dissolve into the water (due to a concentration gradient); once dissolved, it is forced to permeate through the filter cartridge due to a pressure gradient (applied by the vacuum pump). This way, all air (dissolved or not), is over time removed to an acceptable level from fluid circulation system 314. The small change in volume due to the removal of air may be compensated for by syringe 175, and by a slight deformation of the acoustic membrane of probe 310, which is flexible.

Further, if additional (non-degassed) water is added to the system, such as that required to adjust the probe position and acoustic membrane height for proper treatment, this water will increase the gas content of the existing water somewhat, which will in turn be taken out over the next few seconds be the degasser. As long as the added water volume is small (<50 cc, typical syringe volume) with respect to that already present in the waterpath (approximately 450 cc), the dissolved oxygen content of the coupling fluid does not change noticeably to negatively affect the treatment.

Although the invention has been described in detail with reference to certain illustrated embodiments, variations and modifications exist within the spirit and scope of the invention as described and defined in the following claims.

The invention claimed is:

1. An apparatus for treating tissue, the apparatus comprising,
   a probe including
      a transducer which is positionable proximate to the tissue to be treated, and configured to provide HIFU energy to the tissue to be treated and to sense ultrasound energy,
      a positioning member coupled to the transducer and configured to position the transducer relative to the tissue to be treated, and
      a fluid inlet and a fluid outlet, both the fluid inlet and the fluid outlet being in fluid communication with a fluid pathway including an area adjacent a face of the transducer; and
   a fluid circulation system in fluid communication with the fluid inlet and the fluid outlet of the probe, the fluid circulation system including
      a pump configured to circulate a fluid throughout the fluid circulation system and the fluid pathway of the probe;
      a chiller configured to reduce a temperature of the fluid;
      a degasser which is configured to remove dissolved gases from the fluid;
      a fluid adjustment member including a reservoir in which the fluid passes, the fluid adjustment member being configured to both add additional fluid to the fluid circulation system and remove fluid from the fluid circulation system, the fluid adjustment member being in fluid communication with the reservoir; and
      a first fluid circuit and a second fluid circuit, the first fluid circuit being in fluid communication with the fluid pathway of the probe and the reservoir and the second fluid circuit being in fluid communication with the degasser and the reservoir such that fluid in the second circuit may pass into the first circuit through the reservoir and fluid in the first circuit may pass into the second circuit through the reservoir.

2. The apparatus of claim 1, wherein the pump is a part of the first fluid circuit and a second pump is a part of the second circuit, the second pump configured to circulate the fluid through the second circuit.

3. The apparatus of claim 2, further comprising a controller operably coupled to the transducer and to the positioning member, the controller being configured to position the transducer with the positioning member and to operate the transducer in an imaging mode wherein images of the tissue to be treated are obtained from ultrasound energy sensed by the transducer and in a therapy mode wherein a plurality of treatment sites are treated with a HIFU Therapy with the transducer.

4. The apparatus of claim 2, wherein the pump, the second pump, and the vacuum pump are electrically connected together such that each is provided electrical power generally at the same time.

5. The apparatus of claim 2, wherein the fluid adjustment member is a syringe.

6. An apparatus for treating tissue, the apparatus comprising,
   a probe including
      a transducer which is positionable proximate to the tissue to be treated, and configured to provide HIFU energy to the tissue to be treated and to sense ultrasound energy,
      a positioning member coupled to the transducer and configured to position the transducer relative to the tissue to be treated wherein the positioning member positions the transducer along a longitudinal axis of the probe and rotationally about the longitudinal axis the probe, a fluid inlet and a fluid outlet, both the fluid inlet and the fluid outlet being in fluid communication with a fluid pathway including an area adjacent a face of the transducer, and an expandable membrane surrounding a first portion of the probe including the area adjacent the face of the transducer wherein the expandable membrane positions the transducer along a direction transverse to the longitudinal axis relative to the tissue; and a fluid circulation system in fluid communication with the fluid inlet and the fluid outlet of the probe, the fluid circulation system including a chiller configured to reduce a temperature of the fluid;

a degasser which is configured to remove dissolved gases from a fluid, wherein the degasser is positioned in series with the fluid inlet and fluid outlet of the probe, and wherein the degasser includes a filter having a plurality of air-permeable fluid conduits through which the fluid passes and a vacuum pump connected to the filter, the vacuum pump reducing the pressure on an outside portion of the air-permeable fluid conduits thereby drawing dissolved air in the fluid through the air-permeable fluid conduits;

a pump configured to circulate a fluid throughout the fluid circulation system and the fluid pathway of the probe, wherein the pump and the vacuum pump are electrically connected together such that each is provided electrical power generally at the same time; and a fluid adjustment member including a fluid reservoir, the fluid adjustment member being configured to both add additional fluid to the fluid circulation system and remove fluid from the fluid circulation system.

7. A method of preparing a HIFU system having a transrectal probe to provide treatment to the prostate area of a patient, the transrectal probe including a fluid pathway which includes an area adjacent a face of a therapy transducer, the method comprising the steps of:

providing a fluid circulation system in fluid communication with the fluid pathway of the transrectal probe, the fluid circulation system including a pump configured to circulate a fluid through the fluid circulation system and the fluid pathway of the transrectal probe and a degasser which is configured to remove dissolved gases from the fluid passing through the degasser, the degasser including a vacuum pump; and electrically coupling the vacuum pump and the pump together such that each receives electrical power at generally the same time.

8. The method of claim 7, wherein the fluid is a non-degassed fluid when introduced into the fluid circulation system.

9. The method of claim 8, wherein the fluid is tap water.

10. The method of claim 8, further comprising the steps of:

waiting a period of time after providing electrical power to the vacuum pump and the pump at least sufficient for the fluid to be degassed to a level below about 3 parts per million;

positioning the transrectal probe relative to the prostate of the patient for providing a HIFU treatment;

imaging the prostate of the patient; and providing the HIFU treatment with the HIFU system.

* * * * *